United States Patent [19]

Bell

[11] Patent Number: 4,485,096

[45] Date of Patent: Nov. 27, 1984

[54] TISSUE-EQUIVALENT AND METHOD FOR PREPARATION THEREOF

[75] Inventor: Eugene Bell, Dedham, Mass.

[73] Assignee: Massachusetts Institute of Technology, Cambridge, Mass.

[21] Appl. No.: 381,978

[22] Filed: May 26, 1982

Related U.S. Application Data

[63] Continuation-in-part of Ser. No. 352,586, Feb. 26, 1982, abandoned, which is a continuation-in-part of Ser. No. 245,536, Mar. 19, 1981, abandoned, which is a continuation-in-part of Ser. No. 972,832, Dec. 26, 1978, abandoned.

[51] Int. Cl.$^3$ ..................... A61K 35/12; A61K 35/36
[52] U.S. Cl. ....................................... 424/95; 424/177
[58] Field of Search .................. 424/95, 177; 435/240

[56] References Cited

U.S. PATENT DOCUMENTS 4,314,380  2/1982  Miyata et al. ............................ 3/1.9

OTHER PUBLICATIONS

Jelenska et al.–Thrombosis & Hemostasis, vol. 44, (Dec. 1980), pp. 161–163.
Bell et al.–J. of Inv. Dermatol., vol. 81, (1983), pp. 25–105.
Worst et al., J. of Nat. Cancer Inst., vol. 53, (1974), pp. 1061–1063.
Bell et al.–Am. Soc. Plastic & Reconstruct. Surgeons, vol. 67, No. 3, (Mar. 1981), pp. 386–392.
Coulomb et al.–J. of Inv. Dermat, vol. 81, (1983), pp. 75–78.
Bell et al.–Science, vol. 211, (1981), pp. 1052–1054.
Bell et al.–Proc. Nat. Acad. Sci., vol. 79, No. 3, (Mar. 1979), pp. 1274–1278.
Sarber et al.–Mechanisms of Ageing & Devel., vol. 17, (1981), pp. 107–117.
Hull et al., J. of Invest. Dermatol., vol. 81, (1983), pp. 436–438.
Hull et al.–J. of Invest. Dermatol, vol. 81, (1983), pp. 429–436.
Coulomb et al.–Brit. J. Dermatol. Supplement 1984.
Sher et al.–Transplantation, vol. 36, No. 5, (1983), pp. 552–557.
Ebendal–Zoon, vol. 2, (1974), pp. 99–104.
Stenzel et al.–Annual Rev. of Biophys. & Bioeng., vol. 3, (1974), pp. 231–253.
Elsdale et al.–J. Cell Biol., vol. 54, (1972), pp. 626–637.
Ehrmann et al.–J. Nat'l Canc. Inst., vol. 16, (1956), pp. 1375–1403.
Michalopoulos et al.–Exptl. Cell Res., vol. 94, (1975), pp. 70–78.
Gey et al.–Exptl. Cell Res., vol. 84, (1974), pp. 63–71.
Hillis et al.–Exptl. Cell Res., vol. 26, (1962), pp. 9–36.

Primary Examiner—Sam Rosen
Attorney, Agent, or Firm—Arthur A. Smith, Jr.; David E. Brook

[57] ABSTRACT

A tissue-equivalent, useful in the treatment of burns or other skin wounds and in the fabrication of prostheses, is disclosed which is prepared from a hydrated collagen lattice contracted by a contractile agent, such as fibroblast cells or blood platelets, to form tissue-equivalent. In one embodiment, a skin-equivalent can be fabricated by growing a layer of keratinocyte cells thereon. Both the keratinocyte cells and contractile agent may be derived from the potential recipient of the skin-equivalent.

29 Claims, 14 Drawing Figures

TISSUE-EQUIVALENT AND METHOD FOR PREPARATION THEREOF

RELATED APPLICATION

This application is a continuation-in-part of Ser. No. 352,586, filed Feb. 26, 1982, which was a continuation-in-part of Ser. No. 245,536, filed Mar. 19, 1981, now abandoned, which was a continuation-in-part of Ser. No. 972,832, filed Dec. 26, 1978, all now abandoned.

TECHNICAL FIELD

This invention is in the field of biology and particularly relates to a living tissue material which can be used to replace skin or in the fabrication of prostheses.

BACKGROUND ART

In many wounds which involve injury to a significant area of human skin, and particularly in the case of massive burns, there is an immediate need to cover the wound with a material which provides some of the functions of skin. These functions involve the reduction of fluid loss, prevention of infections, and reduction of the area for potential scarring.

Approaches which have been employed in solving this problem involve the use of homografts, modified dermal xenografts, synthetic polymeric structures, or reconstituted collagen films. While each of these approaches offers partial success, each also has been replete with serious problems which have not been solved. Particularly significant problems in many of these approaches have been rejection of the skin substitute, particularly in the absence of immunosuppressive agents, or breakdown of the graft by host enzymes.

DISCLOSURE OF THE INVENTION

This invention relates to the discovery that a living tissue can be formed. This living tissue is produced by forming a hydrated collagen lattice, in vitro. This lattice is contracted into a living tissue with a contractile agent incorporated in it. Examples of contractile agents are fibroblast cells and blood platelets.

A skin-equivalent can be produced from this living connecting tissue substrate by plating keratinocyte cells on it and providing for their growth. This skin-equivalent is uniquely different from the previously described artificial skins because its basic organization is like that of skin and its living constituent cells may even be donated by a potential graft recipient.

Small-vessel equivalents can be formed by casting a collagen lattice containing smooth muscle cells around a glass rod or other mandrell and subsequently casting an outer layer of fibroblast cells and then plating an inner layer of endothelial cells. Specific procedures for employing the living tissue-equivalents produced according to this invention in the fabrication of small-vessel equivalents are described in copending application Ser. No. 261,928, filed May 8, 1981.

Gland/organ equivalents can also be formed from the contracted hydrated collagen lattices described herein. For example, glandular cells such as pancreatic $\beta$ cells might be grown on a collagen lattice to produce a pancreas-equivalent capable of boosting insulin supply to the blood stream of a recipient. Similarly, hepatocytes (liver cells) might be grown on a contracted hydrated collagen lattice to produce a liver-equivalent.

Bone-equivalents can be formed from the contracted hydrated collagen lattices. These are produced by incorporating demineralized bone powder into hydrated collagen lattices contracted with fibroblast cells. Thus, the ultimate shape of the bone which differentiates can be predetermined by the shape of the mold in which the materials forming the hydrated collagen lattices are cast.

Thus, it can be seen that the living tissue-equivalents produced according to this invention offer the potential of producing living tissue, gland and organ equivalents of many types and functions. Such equivalents may even be fabricated and stored as inventory until a need to employ them arises.

One of the major advantages of such tissue-equivalents is that they can be employed in a host other than the donor of the cells used to produce the tissue-equivalents without suffering from the serious problems of rejection which might be expected. This is because selection against cells responsible for rejection by a recipient's immune system takes place when the cells used for the fabrication of the living tissue are propagated according to this invention. In addition, certain cells lose their ability to stimulate rejection when preserved in tissue culture under certain conditions according to recent research reports.

In another aspect of this invention, an assay for immune acceptance or rejection can be based upon the tissue-equivalents described above.

BEST MODE OF CARRYING OUT THE INVENTION

Hydrated collagen lattices can be prepared employing collagen derived from rat tail tendon and calf skin collagen. Other sources of collagen including human fetal skin have been employed, and still other sources would be suitable. Solutions of collagen are prepared and maintained under slightly acidic conditions. Lattices are formed by adding fibroblast cells with nutrient medium and base which raises the pH sufficiently to precipitate collagen fibrils from solution. Preparation of hydrated collagen lattices is described in more detail in the following references, the teachings of which are incorporated by reference: Elsdale, T. and Bard, J., "Collagen Substrata For Studies On Cell Behavior," *J. Cell Biol.* 54, 626–637 (1972); Ehrmann, R. L. and Gey, G. 0., "The Growth of Cells on A Transparent Gel of Reconstituted Rat-Tail Collagen," *J. Natl. Cancer Inst.*, 16, 1375–1403 (1956); Emermann, J. T. and Pitelka, D. R., "Hormonal Effects on Intracellular and Secreted Casein in Cultures of Mouse Mammary Epithelial Cells on Floating Collagen Membranes," *In Vitro*, 13, 316–328 (1977); Michalopoulous, G. and Pitot, H. C., "Primary Culture of Parenchymal Liver Cells on Collagen Membranes," *Exp. Cell Res.* 94, 70–78 (1975); Gey, G. 0. Svotelis, M., Foard, M. and Bang, F. B., "Long-Term Growth of Chicken Fibroblasts On A Collagen Substrate," *Exp. Cell Res.*, 84, 63–71 (1974); and Hillis, W. D. and Band, F. B., "The Cultivation of Human Embryonic Liver Cells," *Exp. Cell Res.*, 26, 9–36 (1962).

Fibroblast cells actually used in the experiments described herein as a contractile agent were human foreskin fibroblasts and guinea pig dermal fibroblasts. Fibroblasts from other sources have also be used, and it is believed, in fact, that fibroblasts from any vertebrate animal would be suitable for contracting hydrated collagen lattices. A convenient technique for simultaneously forming the lattice and plating cells therein involves neutralizing an acidic collagen solution maintained in a culture dish with nutrient medium containing fibroblast cells. Upon neutralization, collagen fibrils precipitate from the solution to form the lattice with fibroblast cells homogeneously dispersed therethrough. The cells and collagen lattice are then maintained under conditions which allow the cells to attach to the collagen lattice and to contract it to a fraction of its original size, thereby providing the living tissue.

The incorporation of fibroblast cells into hydrated collagen lattices causes the lattices to contract as trapped water was squeezed out. If the surface on which the lattice was formed is non-wettable, e.g., a hydrophobic plate, the resulting tissue is of regular geometry. On tissue culture plates, some cells migrate from the lattice to the plate surface and contraction of the lattice is not always regular. When a non-wettable surface, such as a bacteriological Petri plate is used, the lattice remains nearly a perfect disc as its radius is decreased by the cells.

Fibroblast cells are found homogeneously dispersed throughout collagen lattices and not merely upon the lattices' surface. This simulates, then, the dermal layer of humans and other mammals.

In the absence of cells, lattices undergo no change in radius. For example, conditioned medium prepared by growing $1 \times 10^6$ human foreskin fibroblast cells for five days in nutrient medium caused no contraction when no cells were present.

Contracted collagen lattices with cells resemble the skin or dermis; even when partially contracted, they have reasonable consistency and can be readily handled. When first made up with cells, the lattices are almost transparent but gradually become opaque as water is excluded and the diameter reduced. After a 20–30-fold decrease in lattice area, they have a firm rubbery consistency, a whitish pink tint, and can be stretched somewhat without being torn or deformed.

The initial diameter of a lattice is determined by the quantity of materials used and by the plate on which it is formed. Thus, maximal contraction is an arbitrary measure, but is related to cell number and protein concentration.

Although most contracted hydrated collagen lattices have been formed as sheets, other shapes can be formed. Tubes, for example, can be formed by forming the contracted lattice in an annular mold, or a glove of skin might be prepared in an appropriate mold.

Human skin keratinocytes, obtained in biopsies, have been deposited on contracted hydrated collagen lattices. The same has been done with keratinocytes cultivated in vitro. Plating of keratinocytes can be done at the time the matrix gel forms, at any time during the period of contraction of the lattice, or any time after contraction has been completed. Within three days after plating suspensions of dissociated keratinocytes, the cells formed a confluent layer on the lattice surface and the process of keratinization begins leading to the formation of a cornified layer which would prevent loss of tissue fluids.

There are other cellular contractile agents, in addition to fibroblast cells. Among these are smooth muscle cells, striated muscle cells and heart muscle cells.

Another contractile agent is blood platelets, which in many cases, can be obtained from the blood of a potential graft recipient. Platelets are separated from whole blood by centrifugation or other techniques for separating blood components from whole blood.

Contraction with platelets is quite rapid with about 80–90% of fluid expression complete by the end of the third hour after casting a collagen lattice containing platelet in most cases. By about six hours, the reaction usually appears to be complete with equilibrium being attained and no further fluid release occurring under conditions of 100% humidity. At this point, typically, 20–80% of the starting fluid volume has been expressed from the collagen lattice with the precise amount depending upon platelet and collagen concentrations and certain other casting medium variables.

The rate of lattice contraction with blood platelets appears to be independent of the type of collagen used. Increasing platelet concentration tends to speed up the rate of contraction and results in a lattice with proportionately less fluid. Increasing the collagen content reduces the rate of contraction and the quantity of fluid expressed. In this regard, platelet contraction is similar to that achieved with the use of living fibroblast cells.

In controlled experiments, it was determined that the inhibitor cytochalasin B inactivates platelets so that lattice contraction does not occur. Cytochalasin B is known to stabilize the discoid shape of platelets preventing pseudopod formation. Lattices cast without platelets or with platelets in the presence of cytochalasin B failed to contract.

The inhibitor colcemid, on the other hand, had no effect on lattice contraction. This was expected since colcemid is known to have no effect on the ability of human platelets to contract fibrin clots.

When thrombin is included in the casting mixture with a sufficient number of platelets, a tissue equivalent is formed from which fluid is quickly excluded. Tissue equivalents formed quickly in this manner have properties somewhat different from those more slowly formed employing platelets alone. For example, their tensile strength is somewhat greater and their fluid content somewhat lower than corresponding tissues formed without thrombin. The quickly formed tissue appears to depend for formation on the concentration of platelets and the presence of thrombin or some other platelet release factor in addition to collagen. Other platelet release factors include fatty acids, ADP, and gamma globulin.

Lattice contraction by a contractile agent such as fibroblast cells or platelets converts the collagen lattice into a tissue equivalent of relatively high tensile strength compared to that of the collagen lattice cast without a contractile agent, when both are maintained under 100% relative humidity conditions. Cast without a contractile agent, the collagen lattice has a consistency similar to fresh gelatine and falls apart on handling. Lattices contracted by platelets or cells can be handled, stretched and sutured without damage.

Tensile strength has been tested by determining the maximum weight for a given time which could be suspended on contracted lattices. In one example, a lattice of 5 ml volume formed in a 5.3 cm diameter dish and contracted to about 2 cm in diameter by fibroblast cells supported 3.5 grams for 7 min. Another lattice also of 5 ml volume in a 5.3 cm diameter dish was contracted from a height of 0.23 cm to one of 0.09 cm with no change of diameter, by platelets, and supported 11 grams for 10 minutes.

It has been noted that tensile strength, and other properties, are a function of many parameters, including the types and amounts of collagen and contractile agent employed and the other additives employed. The work described herein, for example, employed type I collagen. It is known, however, that type III collagen imparts additional tensile strength to skin and blood vessels, and so it would be expected that the use of type III collagen in the collagen lattices described herein would increase their tensile strength. Similarly, the addition of glycosaminoglycans, such as hyaluronic acid, chondroitin 4-sulfate, and dermatan sulfate, have been found to improve tensile strength and water-retention properties.

Antibiotics, such as penicillin, streptomycin and fungizone can also be added, if desired, to prevent microbial infection.

Large as well as small tissue equivalents of excellent coherence can be formed using platelets alone, or the more rapid method employing platelets and an externally supplied platelet release factor, since collagen itself can act as a release factor. The contraction of lattices by platelets appears to occur only in the thickness dimension, so that the final size and shape are determined by the dimensions and geometry of the casting vessel. Thickness at fluid content equilibrium is determined by initial volume of the casting medium as well as by other variables, discussed above.

Experimental grafts on animals discussed herein have employed autologous platelets. Since platelets show considerable antigenicity, it is likely that an allograft would evoke an immune reaction.

Although most of the work described herein relates to the formation of skin-equivalents by growing keratinocytes on contracted collagen lattices, other cell types could be grown on or in lattices. Examples are smooth and striated muscle cells, cartilage, bone cells, pancreatic cells, liver cells, etc.

Bone-equivalents can be prepared by incorporating demineralized bone powder into hydrated collagen lattices contracted with fibroblast cells prepared as described above. The interactions between demineralized bone powder implanted subdermally have been previously described. See Reddi, A. H. and Huggins, C., *Proc. Nat. Acad. Sci. USA*, 69, pp. 1601–5 (1972), the teachings of which are hereby incorporated by reference. Bone equivalents can be prepared by incorporating demineralized bone powder into tissue-equivalent lattices contracted with fibroblasts. This allows the casting of any shape for such a tissue-equivalent and the tissue-equivalent contains the fibroblast cells thought to be responsible for the transformation of the demineralized bone powder to cartilage and bone. Thus, the ultimate shape of the bone and cartilage which differentiates can be predetermined by the shape of the mold into which such materials are cast.

Certain methods and devices have been developed to assist in casting contracted collagen lattices into sheets of controllable dimensions and/or various shapes. With fibroblast cells as the contractile agent, unconstrained collagen lattices typically undergo contraction in all dimensions. However, a sheet whose borders are held fixed contract only in the thickness dimension.

A device suitable for constraining the borders can be made from a sheet of stainless steel mesh of any shape. The desired shape to be cast is cut from the center of the stainless steel mesh after which the excess of the sheet is trimmed off to leave approximately a one-half inch border of mesh around the shape. This forms a frame of stainless steel mesh which can be laid into a pan coated with a non-stick material, such as Teflon ® polytetrafluoroethylene, after which the components used to form the lattice are introduced. When the components are poured and the lattice forms, it fills the lacunae of the steel mesh to which is becomes anchored. As the cellular elements of the lattice compact it by pulling together the collagen fibrils, the volume of the lattice decreases, but because the perimeter is held fixed, the dimension which is reduced is the thickness. In the process, the lattice loses fluid.

The special advantage of the steel frame is that the final size of the tissue equivalent is exactly the size of the inside dimensions of the frame and particularly, the lattice acquires additional strength because of the orientation of cells imposed by the constraining frame. Further, since the dimensions of the lattice do not change in width or length, if it is cast in a rectangular frame, even after it is cut away from the frame, it is possible to apply the epidermal component of skin-equivalent to the dermal equivalent as soon as one day after casting the latter thus shaving at least four days off the time needed to prepare a skin-equivalent graft from a biopsy provided by a patient.

Components of a lattice can be poured into the coated pan to cover the restraining mesh. As the lattice sets, it becomes anchored in the mesh so that on contraction, the length and width remain unchanged. Only the thickness decreases. The ultimate dimension of the thickness is a function of (1) the initial volume of the lattice, (2) the cell concentration and (3) the collagen content. The presence of proteoglycans, such as hyaluronic acid and chondroitin sulfate, result in increased contraction and a decrease in lattice thickness. The rectangular mesh which holds the lattice or dermal equivalent onto which epidermal cells are seeded can be applied intact to a wound requiring skin. While in place, it can be cut away from the inside perimeter of the mesh immediately or at some later time since its presence could help to maintain the integrity of the graft.

Another technique and method which are helpful in anchoring epidermis on the dermal equivalent of skin equivalent preparations is as follows. The dermal equivalent is first cast and a plastic sheet, e.g., Teflon ® polytetrafluoroethylene, through which needle points have been passed and allowed to remain in a regular pattern, is laid over the fresh casting. The plastic sheets and needle points are removed 1-4 days afterward, when the casting is seeded with epidermal cells. This results in the formation of pits into which the epidermal cells flow thereby providing greater surface contact between the epidermis and dermal equivalent.

Follicle and glandular cells, which can be isolated by an enzymatic dissociation technique, might be seeded with the suspensions of epidermal cells to occupy such pits.

A major advantage of the living tissue described herein is the absence of rejection encountered when the recipient is different than the donor of the cells employed in producing the tissue-equivalent. For example, skin-equivalent grafts fabricated with cells other than those of the graft recipient have now been made to animal hosts. Skin-equivalent grafts made up as described above but assembled with cells from female animals of the Sprague-Dawley strain of rats have been grafted to male Fischer rat hosts and allowed to remain in place for various periods. On removal of the grafts, the cells of the dermis are karyotyped (their chromosomes are displayed and catalogued) and their sex determined. Since female cells can be identified by the presence of two X chromosomes, the presence or absence of grafted cells can be positively ascertained. With this procedure, it has been determined that originally grafted cells continue to populate skin equivalent grafts despite their foreignness showing that fibroblasts are not the cells which elicit an immune reaction when a normal skin allograft is made. Whatever the cell types responsible for initiating the homograft rejection reaction, they are not present in the dermal-equivalent grafts. This makes it possible to fabricate skin-equivalent grafts with cells from a source other than the graft recipient and to have grafts in readiness for clinical or emergency use.

It can be generalized that equivalent grafts of any kind which are fabricated without specialized immune cells that are ubiquitous in native tissues will not be rejected since the antigenic determinants responsible for graft rejection are not expressed on the surfaces of cells incorporated into equivalent tissues. Their absence makes it impossible for the immune cells of the host to sense the foreign cells. This provides an opportunity to replace or add types of cells, tissue or organs which a recipient needs, because his own are deficient or absent.

The tissue-equivalents described herein can also be employed as an assay to determine whether any given cell type from a donor will provoke and immune response in the recipient. As described above, there is evidence that fibroblast cells do not contain antigenic determinants which elicit immune response of the type often encountered in inter and intra species transplantations. The tissue-equivalents prepared as described above would be employed by incorporating therein test cells from a donor whose ability to provoke an immune response is unknown. Such tissue-equivalents can then be applied to the donor to determine whether or not an immune response does occur for the test cell type. Thus, the hundreds of cell types of mammalian organisms could be tested employing the tissue-equivalents in such an assay.

The invention can be further specifically illustrated by the following examples.

EXAMPLE 1

Preparation of Tissue-Equivalent by Contracting Collagen Lattices Seeded With Fibroblast Cells Crude collagen solutions were prepared as follows. Frozen rat tails from 450 gm rats were thawed in 70% EtOH for 20 minutes. The tendon bundles were excised in 70% EtOH in a laminar flow hood. Individual tendons were pulled out of the tendon sheath, minced and placed in dilute acetic acid (1:1,000) using 250 ml per tail. This solution was left standing for 48 hours at 4° C. at which point the minced tendons had swelled to occupy the total volume. This viscous solution was centrifuged at 23 k rpm in a Beckman L ultracentrifuge in an SW25 rotor for 1 hour. The supernatant was drawn off and stored at 4° C. as crude collagen solution (Protein "C").

Refined collagen solution was prepared by mixing crude collagen solution with 0.1 M NaOH in a 6:1 ratio to neutralize the acetic acid, upon which collagen precipitated. This solution was centrifuged at 1500 rpm for 5 minutes in a clinical centrifuge. The supernatant was discarded and an equal volume of fresh acetic acid (1:1,000) was introduced to resolubilize the collagen. This solution was stored at 4° C. as refined collagen solution (Protein "R").

Protein concentration was determined by the method of Lowry et al. See Lowry, O. H., Rosebrough, N. J., Farr, N. J. and Randall, R. J., *J. Biol. Chem.*, 193, 265-275 (1951) and Waddel, W. J., *J. Lab and Clin. Med.* 48, 311-314 (1956).

Protein lattices were prepared in 60 mm Falcon bacteriological dishes to which fibroblasts adhere poorly. Each dish contained: 1.0 ml 5X McCoy's 5a medium, 1.0 ml Fetal Calf Serum, 0.25 ml 0.1 M NaOH, 1.5 ml collagen solution, and 1.0 ml fibroblasts suspended in 1X McCoy's medium. The dishes were first filled with the above volume of McCoy's medium, serum and NaOH and then set aside until the fibroblast suspension was prepared. Speed was important in simultaneous addition of collagen solution and fibroblasts since the gel started setting immediately. Dishes were placed in an incubator at 37° C. in a 5% $CO_2$ atmosphere at 100% humidity. Gels incorporating the fibroblasts were completely set after 10 minutes.

The fibroblasts employed were human foreskin fibroblasts, strain 1519, obtained from the Human Genetic Cell Repository at the Institute for Medical Research in Camden, N.J. These cells were grown and maintained in McCoy's 5a modified medium with 20% serum, penicillin, and streptomycin. The cultures were free of mycoplasma. The M.I.T. Cell Culture Center prepared and froze cells of every tenth population doubling level (PDL).

To measure lattice diameters, the dishes were placed on top of a transparent metric ruler on a dark background. Optimum visibility of gel edges was obtained by shining white light horizontally against the edge of the dish. Contracted gels were well formed discs; they showed very slight differences of diameter at various points. The average of the major and minor axes was taken as the diameter.

EXAMPLE 2

Measurement of Contraction of Hydrated Collagen Lattice By Fibroblast Cells

The contraction of a hydrated collagen lattice prepared according to the procedures of Example 1 and containing 570 µg/ml of Protein "C" by $7.5 \times 10^6$ human foreskin fibroblasts, strain 1519, 19th PDL, was determined. Medium was changed in the dish on the first, fourth and eighth days. The data obtained are plotted in FIG. 1 which indicates a 112-fold reduction of lattice area in a little over seven days. Within one day, there had been a seven-fold area contraction.

EXAMPLE 3

Contraction of Hydrated Collagen Lattices Of Different Protein Concentration

The effect of protein concentration in hydrated collagen lattices on contraction of the lattice was determined as follows. Three hydrated collagen lattices were prepared according to the procedures of Example 1 except that each contained a different concentration of Protein "R". Human foreskin fibroblasts, strain 1519, 19th PDL were employed and medium was changed on the fourth day.

Figure 2:
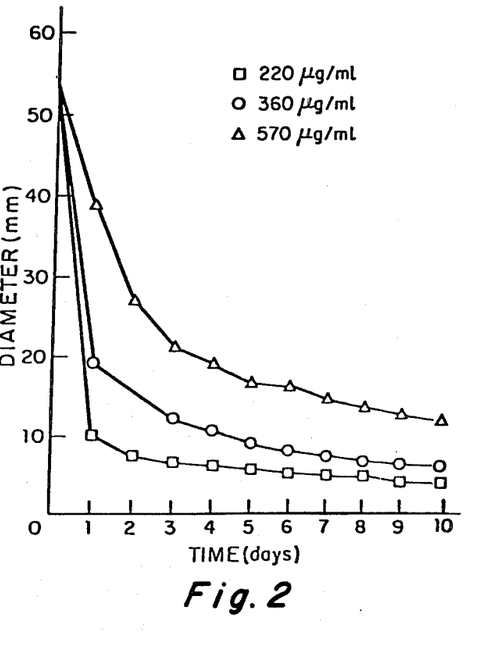
FIG. 2 is a plot of data illustrating the contraction with fibroblast cells of hydrated collagen lattices having different collagen contents.

The data obtained are plotted in FIG. 2 where it can be seen that the rate of lattice contraction varied inversely with gel protein concentration. The lattice areas diminished as time went on.

EXAMPLE 4

Effect of Number of Cells on Contraction Of Hydrated Collagen Lattices

The effect of the number of cells on contraction of hydrated collagen lattices was determined as follows. A number of hydrated collagen lattices containing 720 µg/ml of Protein "R" were prepared according to the procedure of Example 1. Human foreskin fibroblasts, strain 1519, were employed and the medium in each of the cultures was changed in the third, seventh and tenth days.

Controls were employed to which no cells were added. In addition, four series of experiments were run in which varying numbers of cells were added. The data obtained are plotted in FIG. 3 in which each point represents the average of the contraction of three or four lattices. Deviations are not shown because they were all very small ($< \pm 1.0$ mm).

Figure 3:
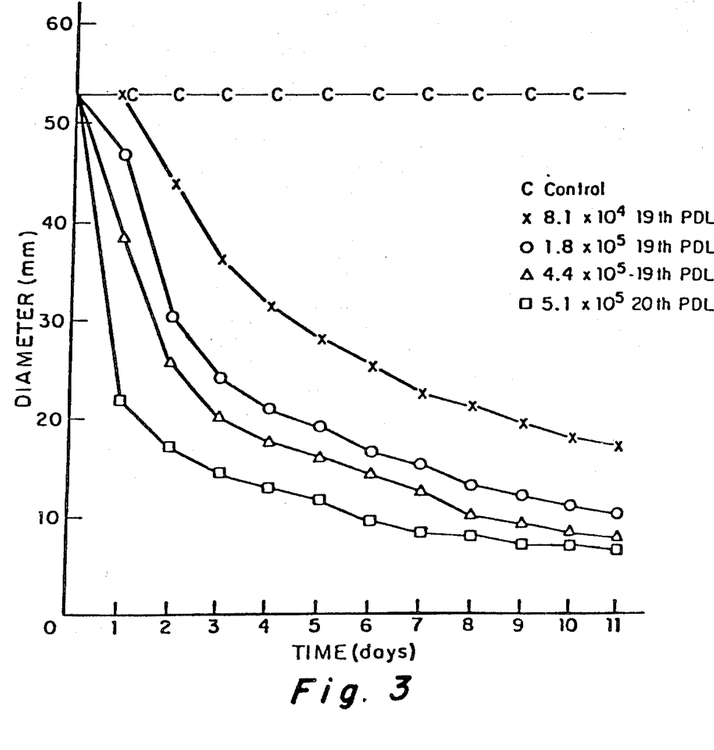
FIG. 3 is a plot of data illustrating the contraction with fibroblast cells of hydrated collagen lattices containing different numbers of fibroblast cells.

As can be seen, the number of cells did have an effect on the rate of lattice contraction but this difference in contraction became less significant as a function of time. Lattice diameters approached a common small number for concentrations above some minimum value. Below the minimum value, the relationship between rate of lattice contraction and cell number was distinctly non-linear. The lattices with $8.1 \times 10^4$ cells did not begin to contract for 24 hours. These sparsely populated lattices lagged well behind the more densely populated ones throughout the period of the experiments.

EXAMPLE 5

Contractile Capacity in Hydrated Collagen Lattices Of Cells Of Different PDL

The contractile capacity in hydrated collagen lattices of cells of different population doubling level (PDL), that is cells which had undergone different numbers of cell divisions, was determined as follows. Cultures were formed of hydrated collagen lattices prepared according to the procedures of Example 1 and containing 720 µg/ml Protein "R". Medium was changed on the third, seventh and tenth days.

Control cultures contained no cells. In addition, a series of experiments with cells of different PDLs was carried out.

Figure 4:
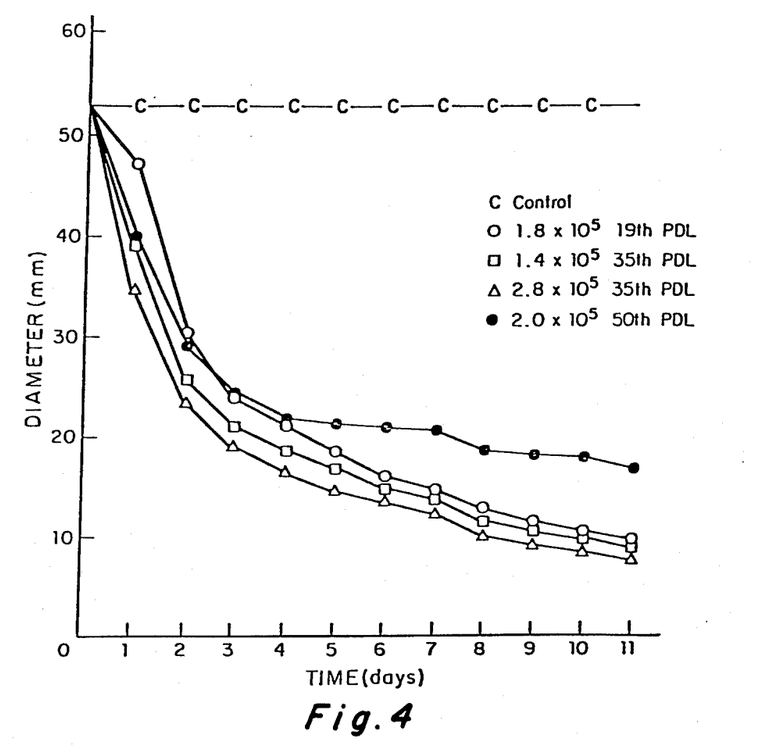
FIG. 4 is a plot of data indicating the contractile capacity of fibroblast cells on hydrated collagen lattices employing cells of different population doubling levels.

The data collected are plotted in FIG. 4 in which each point represents the average of three or four lattice contractions. Deviations were $< \pm 1.0$ mm. As can be seen, cells of the 35th PDL performed as well as those of the 19th PDL, but cells of the 50th PDL were unable to contract lattices at a commensurate rate.

EXAMPLE 6

Effect of Cytochalasin B On Capacity Of Cells To Contract A Hydrated Collagen Lattice The effect of the inhibitor cytochalasin B on the capacity of cells to contract a hydrated collagen lattice was determined as follows. Hydrated collagen lattices were prepared according to Example 1 which contained a Protein "C" content of 570 µg/ml. Fibroblast (human foreskin, strain 1519, 19th PDL) cell concentration in the cultures was $5.0 \times 10^5$. 10.0 µg/ml cytochalasin B was added to each culture and medium was changed on the fourth and eighth days.

Figure 5:
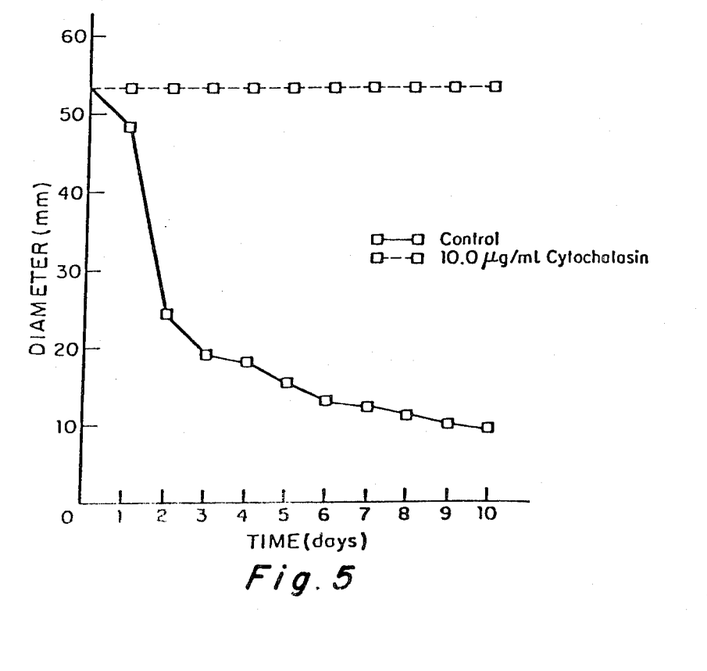
FIG. 5 is a plot of data illustrating the effect of 10.0 $\mu$g/ml of the inhibitor cytochalasin B on the capacity of fibroblast cells to contract a hydrated collagen lattice.

Data obtained are plotted in FIG. 5, and as can be seen, this concentration of cytochalasin B completely blocked lattice contraction even at the relatively high cell concentration employed.

EXAMPLE 7

Effect of Colcemid On Collagen Lattice Concentration

Figure 6:
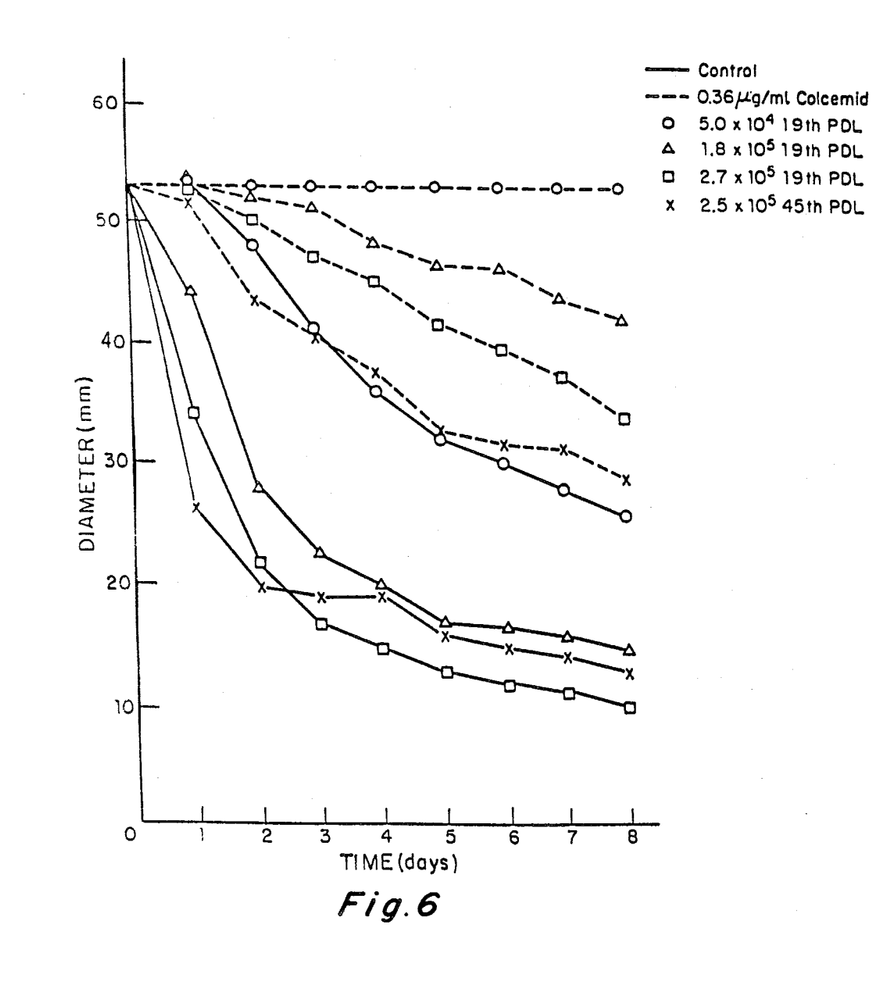
FIG. 6 is a plot of data illustrating the effect of 0.36 $\mu$g/ml of the inhibitor colcemid on the capacity of fibroblast cells to contract a hydrated collagen lattice; and, FIG. 7 is a plot of data illustrating the effect of cytosine arabinoside on the capacity of fibroblast cells to contract a hydrated collagen lattice.

The effect of the inhibitor colcemid on protein lattice contraction was determined as follows. Cultures containing hydrated collagen lattices prepared according to the procedures of Example 1 which contained 570 µg/ml of Protein "C" 0.36 µg/ml colcemid was added to each of these except for the controls which contained no colcemid. The same number of cells was added to both test cultures and control cultures, and data obtained are plotted in FIG. 6. As can be seen, the 45th PDL cells outstripped the performance of 19th PDL cells, while 45th PDL untreated cells lagged behind the 19th PDL untreated cells. It is clear that colcemid can be used to regulate the rate and extent of contraction of the lattices.

EXAMPLE 8

Figure 7:
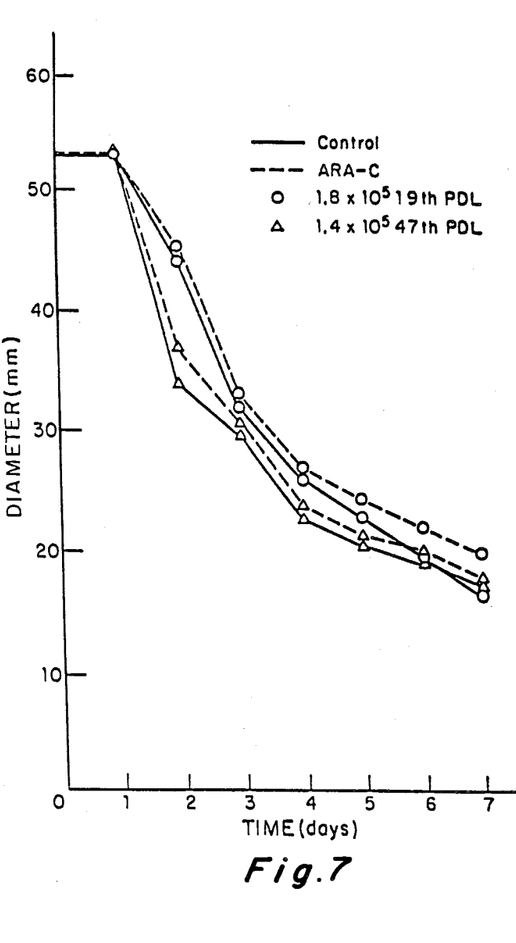

Effect of Cytosine Arabinoside On Collagen Lattice Contraction By Cells Of Different PDL The effect of 1.0 µg/ml of cytosine arabinoside on protein lattice contraction by cells of different PDL level was tested as follows. Cultures containing hydrated collagen lattices containing Protein "C" in a concentration 570 µg/ml were prepared. Human foreskin fibroblasts, strain 1519, of the 19th PDL or 47th PDL were added to both controls containing no cytosine arabinoside and test cultures containing cytosine arabinoside. Data obtained are plotted in FIG. 7, where it can be seen that the 47th PDL cells outperformed the lower PDL cells even though they were fewer in number. In these experiments cytosine arabinoside was used to block DNA synthesis and thereby keep the number of cells in the lattice constant.

EXAMPLE 9

Formation of Skin-Equivalent Employing Human Foreskin Fibroblasts and Keratinocytes A hydrated collagen lattice was prepared according to the procedures of Example 1 which contained 500 µg/ml of Protein "C". Human foreskin fibroblasts obtained in a biopsy were removed from a culture plate with a solution of EDTA and trypsin. The suspension of single cells was centrifuged to pellet the cells, after which the cells were resuspended in culture medium and then deposited on top of the hydrated collagen matrix seven days after the fibroblast cells had been introduced. Within three days, the keratinocyte cells had attached to the lattice substrate and the process of keratinization began leading to the formation of an impervious cornium. Histological observations were made by means of electron microscopy.

EXAMPLE 10

In Vivo Studies With Skin-Equivalent Employing Guinea Pig Skin Fibroblasts and Keratinocytes Skin biopsies were taken from guinea pigs and dermis was separated from epidermis surgically. Dermis was dissociated enzymatically into constituent cells which were plated onto tissue culture dishes and allowed to undergo proliferation. Cells from each experimental animal were grown in separate dishes so that their identity was preserved. Tissues were made up in vitro by forming contracted-hydrated collagen lattices according to the procedures of Example 1 except employing fibroblasts from the guinea pigs. Some of the lattices, after contraction, were plated according to Example 9 with epidermal cells or keratinocytes taken from second biopsies so that keratinocytes as well as fibroblasts in each graft were from the animal which was to become the recipient of the graft.

Grafts of these skin-equivalents were made to the dorsum of the experimental animals (guinea pigs), and it was found that such grafts were thoroughly integrated at all levels within one week. From below, they had become vascularized; at the level of the dermis, collagen fibrils of the graft were interwoven with those of the surrounding host tissue. In histological sections, the grafts could be distinguished by their high fibroblast cell density and by the reduced degree of birefringence as compared with that of surrounding skin when viewed through a polarization microscope. Even those grafts hot provided with epidermis were completely covered with an epidermal cell layer (keratinocytes) many cells deep. The layer was continuous with that of the adjacent host skin. It was clear also that dermal wound contraction was inhibited by the presence of the skin-equivalent graft just as it is when an autograft is made.

EXAMPLE 11

In Vivo Studies With Skin-Equivalent Employing Rat Skin Fibroblasts, Dermal and Epidermal Cells Formation of Dermal-Equivalent A small biopsy from a potential graft recipient was cut into 1.0 mm$^2$ fragments. Fibloblasts grew out of the fragments and populated the Lux tissue culture dish, and after 4–7 days, the fragments were removed and discarded or transferred to new plates. The cells on one or more plates were allowed to propagate until they became nearly confluent, at which time the cells were removed by treatment with trypsin, washed, and thereafter propagated in tissue-culture flasks. About $5 \times 10^4$ cells were needed for each square centimeter of dermal equivalent, and an appropriate number of cells was cast by removing them from the substrate with trypsin after which they were suspended and combined with a collagen solution, rat serum, and tissue-culture medium. Collagen was obtained by extracting rat tail tendons in 0.02 M acetic acid and purifying by centrifugation. When kept at an acid pH and a protein concentration of 1.5 mg/ml, the collagen was a viscous slightly opalescent solution. It consisted only of collagen type I with no contaminating proteins detectable by SDS polyacrylamide gel electrophoresis. At the moment the collagenwas combined with the cells and other ingredients, the pH was adjusted to 7.2 with NaOH, which caused the collagen to come out of the solution in the form of fibrils. As this occurred, a gel or lattice in which fluid was trapped formed. The cells in the lattice were more or less uniformly distributed through it. By a process of active compaction of collagen fibrils by the cells, the lattice was transformed into a tissue of firm consistency. The result was loss of trapped fluid and a many-fold decrease in volume of the original lattice. A tissue resulted which constituted a dermal-equivalent (DE).

Addition of Epidermis

Epidermal cells dissociated from the biopsy fragments by means of trypsin were distributed as a suspension on the dermal equivalent. In 2–4 days, the epidermal cells formed a continuous sheet that covered the dermal substratum. Within this time, the confluent sheet of cells began to differentiate. Desmosomal junctions, tonofilaments, and keratohyalin granules were apparent, and the process of keratinization proceeded leading to formation of an impervious stratum corneum. The entire process would occur in vitro on the DE if permitted. However, in this work, the living, two-layered tissue was considered ready for grafting as soon as the epidermal cells formed a confluent sheet which served as a skin-equivalent (SE).

Skin-equivalents were grafted to a large number of rats with the following results. First, by 3–5 days after implantation, vascularization of the graft had begun and continued rapidly with no necrosis or ischemia occurring. Second, with few exceptions, the graft inhibited would contraction. When the graft was made, the periphery of normal skin adjacent to the graft was tatooed to mark the limits of the grafts, a procedure which enabled the monitoring with time of the dimensions of the graft. The exceptions to inhibition of wound contraction may have been due to inadequate initial coverage of the dermal equivalent by the epidermis, to dislodgement of the graft by the animal, or to formation of an inadequate lattice which was a function of the quality of the collen preparation used.

In one study of thirty-one such grafts examined at the time the bandage was removed (9–14 days), seven inhibited wound contract completely, fifteen blocked would contraction by 75% or more, and twenty-three blocked it by 50% or more.

In another study of fifty-two grafts, wound contraction was blocked in at least 75–80% of the grafts.

Although a number of grafts showed a decrease in size with time, most were stabilized by sixty days and none were rejected. Grafts of large size (approximately 8×12 cm) with good epidermal coverings, effectively blocked wound contraction (75% or more) and took well as replacements for burned skin.

Grafts persisted for long periods, the longest having been in place for over two years.

In addition to becoming well vascularized, the matrix of the dermal equivalent underwent considerable remodeling during the first few months after grafting. Changes in its structure were studied by examing the birefringence of histologic section from which it was apparent that the matrix exhibited birefringence by one week after grafting, a phenomenon not observed in granulation tissue of comparable age. Whereas the birefringence increased in intensity with time, the pattern, generally, was not one of the basket-weave configuration characteristic of normal dermis. However, by ten weeks in the transition region where the graft meets normal tissue, the basketweave pattern had begun to develop.

In vivo, the epidermis hypertrophies, and even ten weeks after grafting, was considerably thicker than adjacent normal tissue. Tongues or pegs or epidermis were seen penetrating the dermal equivalent. Externally, for a period of several months, the epidermis appeared somewhat scaley, and the graft had a reddish tint. By about three months, grafts were smooth and pinkish in color resembling normal skin of the albino rat but lacking hair. A degree of scaliness persisted even to seven months which might be attributed to the absence of sebaceous glands.

EXAMPLE 12

Preparation of Tissue-Equivalent By Contraction of Collagen Lattice With Platelets Outdated platelet concentrates were obtained from the Red Cross Blood Center in Boston, Mass. Rat and pig tail tendon collagens were extracted as described in Example 1; pigskin collagen was supplied by Dr. Paul Ehrlich of the Shriners' Burns Institute of Boston; and telogen, a bovine collagen, was obtained from Collagen Corporation, Palo Alto, Calif. Collagen concentrations were determined using a modification of the method of Waddel. See Waddel, W. J., *J. Lab and Clin. Med.* 48, 311-14 (1956). The formula employed was:

$\mu g/ml = O.D.\ 215 - O.D.\ 225/64.6.$

The platelet concentrate, concentrated to 60x as obtained from the Red Cross, was further concentrated by centrifugation for 50 minutes at 500 rpm in an IEC PR-2 centrifuge using a 253 rotor at 4° C. to remove red blood cells. The supernatant was then centrifuged an additional 50 minutes at 1500 rpm using the same rotor to concentrate the platelets. Supernatant was drawn off and used to resuspend the platelet pellets obtained. The absolute platelet concentration varied from one experiment to the next depending upon the platelet concentrations in the blood of the donors, but all concentration values within each experiment are based on the use of one or pooled samples which are concentrated and then diluted. A 1x platelet concentration is equivalent to the concentration of platelets in 1.0 ml of blood.

Platelet lattices were cast by combining, in order, the following: 2.3 ml DMEM 1.76x medium, (Flow Laboratories), 1.5 ml rat tail tendon collagen, 0.25 ml 0.1 N NaOH (the concentration of NaOH needed to neutralize the collagen varied slightly depending upon the acidity of the collagen preparations used), and 0.45 ml FBS (Flow Laboratories). This mixture was poured into a 60 mm Falcon 0007 Petri dish with 0.5 ml of a 5x platelet concentrate applied in small drops on the dish surface. Alternately, all ingredients were combined in a separate vessel and poured into the empty Petri dish. The resulting lattices were incubated at 37° C. in a 90% air/10% $CO_2$ atmosphere of 100% humidity. Lattice thickness was controlled by increasing or decreasing the total lattice volume cast. No differences were observed in rates of lattice contraction as a function of casting procedure.

The rates of contraction were determined by drawing the fluid released by the lattice into a 1 ml pipette at first, and larger ones later, and then recording the volume of withdrawn fluid after which the withdrawn fluid was returned to the dish. These measurements were repeated hourly until the lattice had contracted maximally. In those lattices having a platelet concentration of 1x or lower, the lattice edges were first detached from the dish using a fine scalpel to free fluid trapped beneath the lattice for measurement. Because a lattice will release additional fluid when torn, care was taken to avoid damaging the lattice to obtain measurements of fluid released only by platelet contraction. Experiments were also conducted to determine the effect of the addition of thrombin (Sigma Chemicals) by spotting thrombin and platelet concentrate onto the Petri dish in discrete droplets prior to the addition of the combined DMEM collagen, NaOH and FBS.

Figure 8:
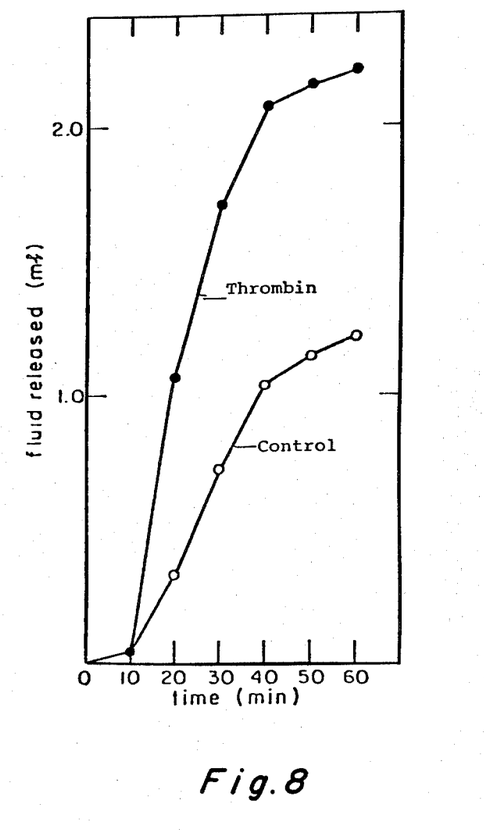
FIG. 8 is a plot illustrating the effect of thrombin on the contraction by platelets of collagen lattices at a thrombin concentration of 4.0 units/ml.

FIG. 8 is a plot of data obtained which illustrate the effect of thrombin on the contraction by platelets of collagen lattices when the thrombin concentration was 4.0 units/ml.

Figure 9:
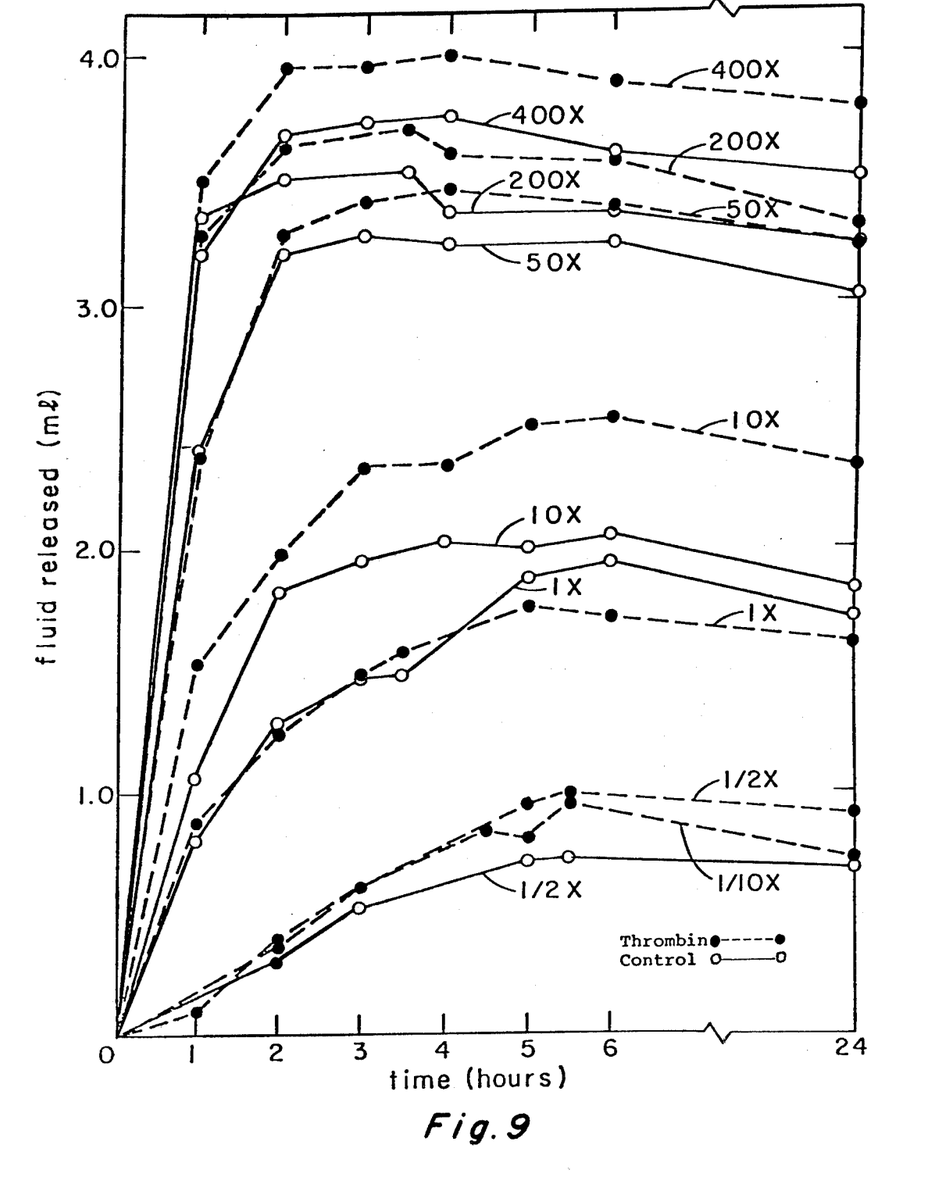
FIG. 9 is a plot illustrating collagen lattice contraction as a function of a platelet concentration and the presence of thrombin at a concentration of 4.0 units/ml.
Figure 10A:
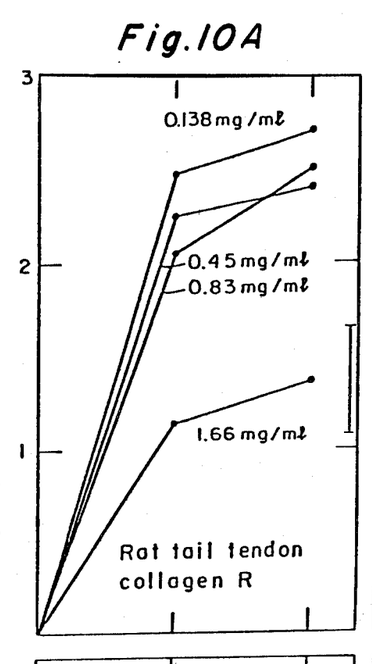
FIGS. 10A–10D are plots illustrating lattice contraction of collagen lattices as a function of the type and concentration of collagen employed; and, FIG. 11 is a plot illustrating the effects of the inhibitors cytochalasin B and colcemid on the contraction of hydrated collagen lattices by platelets.
Figure 10B:
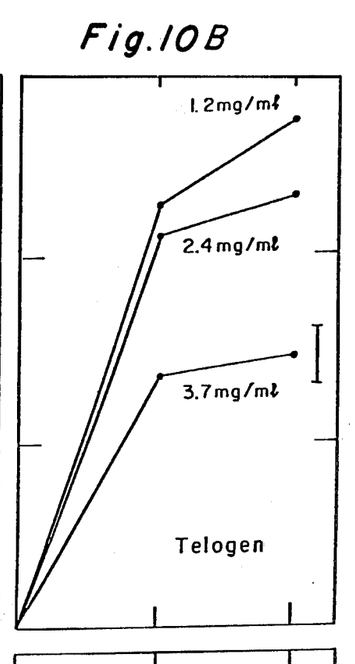
Figure 10C:
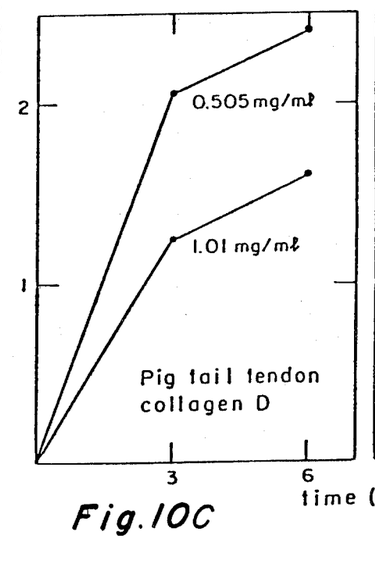
Figure 10D:
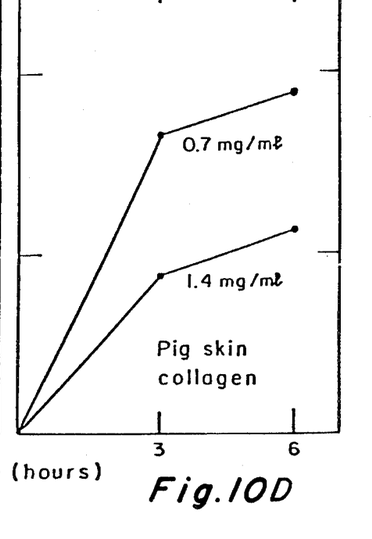

FIG. 9 is a plot illustrating the lattice contraction obtained as a function of platelet concentration and the presence of thrombin at a concentration of 4.0 units/ml.

As can be seen, the reaction is quite rapid. At a platelet concentration of 1x, 80-90% of the total fluid which will be expressed has taken place by the third hour after casting of the lattice. By six hours, the reaction is essentially complete and equilibrium is attained; that is, no further fluid release is observed under conditions of 100% humidity. At this point, 20-80% of the initial fluid volume has been expressed from the lattice, with the precise amount depending upon platelet and collagen concentrations and on other casting medium variables. The process of platelet lattice contraction results in the formation of a tissue-equivalent of relatively high tensile strength compared with that of a collagen lattice cast without platelets.

Figure 1:
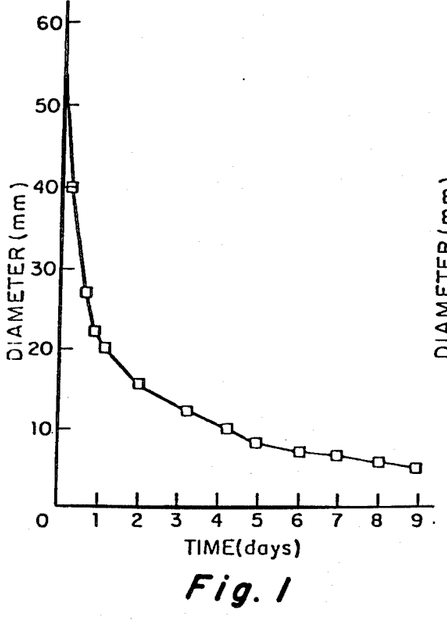
FIG. 1 is a plot of data illustrating the contraction with fibroblast cells of a hydrated collagen lattice.

When thrombin is included in the casting mixture with a sufficient number of platelets, the tissue equivalent forms more quickly as indicated by FIG. 1. The tissue-equivalent containing thrombin has properties somewhat different from those cast without it, its tensile strength being somewhat less and its fluid content lower. Tensile strength was measured by tying gram weights to tissue equivalents after casting and measuring breaking time.

The rate of contraction of platelet lattices is related to the concentration of platelets. Increasing the platelet concentration speeds up the rate of lattice contraction and results in a lattice with proportionately less fluid, as can be seen in FIG. 9.

EXAMPLE 13

Effect of Protein Concentration And Type on Contraction By Platelets

The effect of protein concentration and source on contraction of lattices by platelets was determined by employing collagen from different sources in different concentrations, but otherwise following the procedures of Example 12. The resulting data are plotted in FIGS. 10A–10D.

As can be seen, increasing the collagen content of the casting medium reduces the rate of contraction and quantity of fluid expressed. These results correspond generally to those obtained when fibroblasts were used as the contractile agent.

Collagen from the four different sources employed functioned similarly, except that telogen offerred considerably less resistance to contraction than collagen from the other three sources.

EXAMPLE 14

Effect of Inhibitors Cytochalasin B And Colcemid On Contraction of Collagen Lattices By Platelets The effects of the inhibitors cytochalasin B and colcemid on the capacity of platelets to contract hydrated collagen lattices was determined following the general procedures of Example 12, except as follows.

Cytochalasin B (Sigma Chemicals) and colcemid (CIBA Pharmaceutical Company) were added directly to the concentrated DMEM medium to give final concentrations in the 5 ml lattice volume of 10 µg/ml and 0.5 µg/ml, respectively. Data obtained are plotted in FIG. 11.

Figure 11:
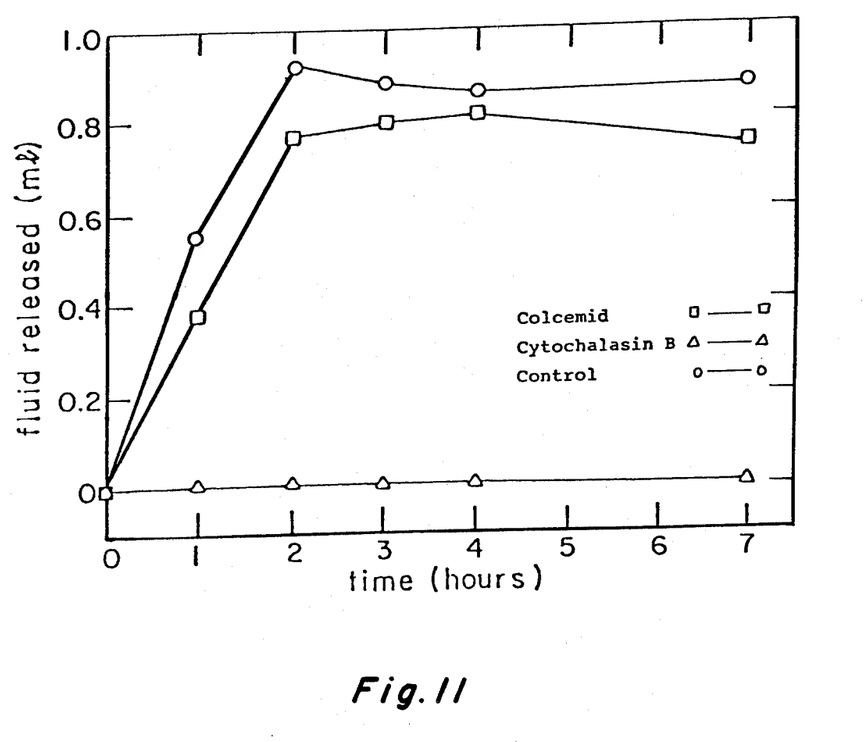

As can be seen, lattices cast with platelets in the presence of cytochalasin B failed to contract. Colcemid, on the other hand, had no apparent effect on lattice contraction; this was expected since Colcemid is known to have no effect on the ability of human platelets to contract fibrin clots. Cytochalasin B, on the other hand, stabilizes the discoid shape of platelets and prevents pseudopod formation.

EXAMPLE 15

Rabbit Grafts

Tissue-equivalents formed from hydrated collagen lattices contracted by platelets and suitable for grafting to the ears of rabbits were prepared as follows. Platelets were collected from 10 ml of rabbit blood taken from the potential graft recipient by heart puncture, and concentrated by differential centrifugation as described in Example 12. Rabbit platelet gels were cast, also following the procedures of Example 12. After contraction, the lattices were seeded with epidermal cells derived from a biopsy from the same rabbit following the procedures of Example 11.

The anesthetized rabbit was prepared for grafting by clipping the hair over the graft site. The graft bed was outlined, and tatoo marks were placed just outside the periphery of the outline. The site was washed with 70% ethanol and all tissue down to the fascia overlying the cartilege was removed. The tissue-equivalent was freed from the dish and placed on the graft bed with the edges of the graft slightly overlapping the edges of the graft bed. The graft was overlaid with tulle gras prepared by impregnating Telfa pads with vaseline. Telfa pads soaked in Earle's salt solution were placed over the tulle gras. A foam pad was used in the ear to hold it in shape and the ear was bandaged with three-inch Elastoplast. To prevent the rabbit from removing the bandage, both ears were taped together with three-inch Elastoplast. The bandages were removed seven days after grafting. The rabbit was fitted with an Elizabethan collar to prevent scratching for another two days.

The grafted region together with a border of normal skin was excised as a single piece from the rabbit ear and immersed in 10% formalin in 0.03 M phosphate buffer. The skin was fixed overnight, rinsed with distilled water, dehydrated in ethanol, cleaned in amyl acetate followed by toluene and embedded in Paraplast t. Seven micron sections were cut using a rotary microtome and these were stained with hematoxylin and eosin.

Grafts were accepted and inhibited wound contraction in all experiments. Grossly, the grafts appeared whiter than surrounding skin, the surface being somewhat scaly and lacking hair. Even after six weeks, a small centrally located scab remained.

A graft which had been in place for six weeks was examined histologically in part to determine the degree to which the graft was infiltrated by fibroblasts from surrounding tissue. The density of fibroblasts in the graft was considerably greater than that of the adjacent tissue. The graft was distinguished from surrounding tissue by the reduced level of birefringence noted viewed under a light microscope. Vascularization in the graft appeared to be greater than in adjacent tissue. The graft was further distinguished from surrounding tissue by the absence of secondary derivatives, that is, hair follicles and sebaceous glands. The epidermal covering of the graft was markedly hypertrophied.

EXAMPLE 16

In Vivo Studies of Rejection of Skin-Equivalent in Rats

Formation of Skin-Equivalent

Small pieces of skin were removed from the backs of female Fischer-344 rats (Charles River Breeding Labs.). These biopsies were trimmed of extraneous tissue, cut into 2–3 mm$^3$ pieces and dried down onto the surface of Lux tissue culture dishes. The fibroblasts which grew out of the biopsies were culturedin Dulbecco's modification of Eagle's Minimal Essential Medium (DMEM) supplemented with 10 percent fetal calf serum, penicillin, streptomyccin and fungizone (Flow Laboratories) in a 10 percent $CO_2$ atmosphere at 37° C.

Collagen lattices were prepared following the procedures of Example 11. Briefly, 2–8×10$^5$ fibroblast cells were combined in a 100 mm plastic dish with concentrated DMEM plus 10 percent fetal calf serum, antibiotics and 6 mg of rat tail collagen in a 1:1000 dilution of acetic acid in water. Within a week the fibroblasts had contracted the collagen lattice and a suspension of epidermal cells dissociated from a fresh biopsy was layered onto the surface of the lattice. Cholera toxin at 10$^{-10}$M, epidermal growth factor at 20 µg/ml and hydrocortisone at 0.4 µg/ml were added to the medium to promote the growth of epidermal cells and the dishes were moved to a 5 percent $CO_2$ atmosphere. Within a week the epidermal cells formed a confluent sheet on the surface of the collagen lattice and the skinequivalent was ready for grafting.

To test allografts, lattices were prepared with cells from the female Sprague-Dawley rats and implanted onto male Fisher rats.

Grafting Procedure

Male Fischer rats weighing approximately 350–400 g. were anesthetized with sodium phenobarbital. A graft bed approximately the same size as the lattice was prepared by removing the full thickness of the skin from the back of each animal. The lattice was placed in the wound and covered with a vaseline-impregnated Telfa pad and a Telfa pad soaked in Earle's salt Solution. These bandages were covered by wrapping the body with several layers of Elastoplast. At time intervals ranging from nine days to thirteen months after the graft was originally applied, the animals were again anesthetized and the entire graft was excised. Half of the graft was fixed in phosphate-buffered formalin, dehydrated in ethanol, and embedded in paraffin. A central portion of the other half of the graft was trimmed of underlying fat tissue, cut into 2–3 $mm^3$ pieces and placed in tissue culture to allow the resident fibroblasts to grow out.

Preparation of the Karyotypes

The population of fibroblasts which grew out of the grafts was subcultured to obtain three to six T-150 flasks of rapidly dividing cells. The fibroblasts were treated with colchicine at 2 $\mu$g/ml for four hours, shaken off the flasks, swollen in hypotonic medium (1 part DMEM to 3 parts distilled $H_2O$), air-dried onto glass slides, and stained with aceto-orcein. Twenty to thirty complete chromosomal spreads for each time point were photographed and kayrotypes prepared to determine the proportion of female cells in the total population of fibroblasts.

Drafts with Sprague-Dawley female cells were received and retained by male Fisher hosts as determined by the presence of female cells in the graft 1–2 months afterward.

INDUSTRIAL APPLICABILITY

The skin-equivalent described herein is suitable for the treatment of a wound to the skin of a human being or other mammal. It is particularly suitable for massive burns.

Contraction of hydrated collagen lattices by fibroblast cells can also be used as an assay for measuring fibroblast function, including contractile power.

In addition to skin-equivalents, wound dressings, etc., the tissue-equivalent can be tailored for other applications. For example, contracted collagen lattices could be employed as carriers for other cell types, such as pancreatic islet cells, in the production of a tissue having pancreatic function, particularly one produced from cells obtained from the potential recipient.

Additionally, tubes or other shapes might be prepared from contracted lattices containing fibroblasts, heart muscle cells, or other cells, to form living prostheses. Such prostheses may be even further treated, such as by irradiation or with chemicals, to convert them to non-living but biocompatible prostheses.

EQUIVALENTS

Those skilled in the art will recognize, or be able to ascertain using no more than routine experimentation, other equivalents for the specific reactants, catalysts, steps, techniques, etc., described herein. Such equivalents are intended to be included within the scope of the following claims.

I claim:

1. A method of producing a tissue-equivalent, comprising:

a. combining a collagen solution with a contractile agent under conditions to form a gel mixture having said contractile agent dispersed within said gel mixture; and then b. maintaining the gel mixture prepared in step (a) under conditions which permit the contraction of said gel mixture to form a tissue-equivalent.

2. A method of claim 1 additionally including adding living tissue cells into or onto said tissue-equivalent.

3. A method of claim 1 or 2 wherein said contractile agent comprises fibroblast cells.

4. A method of claim 1 or 2 wherein said contractile agent comprises blood platelets.

5. A method of claim 1 or 2 wherein said contractile agent comprises smooth muscle cells.

6. A method of claim 1 or 2 wherein said contractile agent comprises striated muscle cells.

7. A method of claim 1 or 2 wherein said contractile agent comprises heart muscle cells.

8. A tissue-equivalent formed according to the method of claim 1.

9. A tissue-equivalent formed according to the method of claim 2.

10. A method of preparing a living tissue-equivalent, comprising:

a. forming an acidic solution of collagen;

b. combining contractile cells and nutrient medium with said acidic solution of collagen;

c. raising the pH of said solution of collagen to a level sufficient to precipitate collagen fibrils into a hydrated collagen lattice containing said contractile cells; and d. maintaining said lattice and said contractile cells under conditions sufficient for said cells to contract said collagen lattice thereby forming a living tissue-equivalent.

11. A method of claim 10 wherein steps b and c are done simultaneously.

12. A living tissue-equivalent formed by the method of claim 11.

13. A method of forming skin-equivalent, comprising:

a. forming a hydrated collagen lattice incorporating a living cellular contractile agent therein;

b. maintaining said lattice and said contractile agent under conditions sufficient for said agent to contract said collagen lattice to form living dermal-equivalent;

c. plating keratinocyte cells upon said dermal-equivalent; and d. maintaining said dermal equivalent under conditions sufficient for growth of said living cellular contractile agent and said keratinocyte cells to thereby produce a skin-equivalent.

14. A skin-equivalent, comprising:

a. a hydrated collagen lattice contracted with a contractile agent; and b. keratinocyte cells supported upon said contracted hydrated collagen lattice.

15. A method of treating a wound to the skin of a donor, comprising:

a. culturing fibroblast cells, in vitro, said fibroblast cells being derived from the donor;

b. forming a hydrated collagen lattice incorpotating said cultured fibroblast cells and maintaining said lattice and said cells under conditions whereby said fibroblast cells attach to said collagen lattice and contract it into a living tissue-equivalent; and c. transplanting said living tissue-equivalent as a graft at the wound site of said donor.

16. A method of claim 15 additionally including growing a layer of keratinocytes upon said living tissue-equivalent prior to transplanting it.

17. A method of forming a biocompatible prosthesis for a potential recipient, comprising:
   a. forming a hydrated collagen lattice incorporating a contractile agent obtained from said potential recipient; and
   b. maintaining said lattice and contractile agent under conditions sufficient to contract the hydrated collagen lattice into biocompatible prosthesis.

18. A method of forming a biocompatible prosthesis for a potential recipient, comprising:
   a. forming a hydrated collagen lattice incorporating a contractile agent obtained from a donor other than said potential recipient; and
   b. maintaining said lattice and contractile agent under conditions sufficient for the agent to contract the hydrated collagen lattice into a biocompatible prosthesis.

19. A method of claim 18 wherein said contractile agent comprises fibroblast cells maintained under conditions which eliminate immune response in said potential recipient.

20. A method of claim 17 or claim 19 wherein said contractile agent comprises fibroblast cells.

21. A method of claim 17 or claim 19 wherein said contractile agent comprises blood platelets.

22. A method of claim 17 or claim 19 wherein said contractile agent comprises smooth muscle cells.

23. A method of claim 17 or claim 19 wherein said contractile agent comprises striated muscle cells.

24. A method of claim 17 or claim 19 wherein said contractile agent comprises heart muscle cells.

25. An organ-equivalent, comprising:
   a. a hydrated collagen lattice contracted with fibroblast cells incorporated therein; and
   b. living organ cells thereon or therein.

26. An organ-equivalent of claim 25 wherein said organ cells comprise heart cells.

27. An organ-equivalent of claim 25 wherein said organ cells comprise liver cells.

28. A gland-equivalent, comprising:
   a. a hydrated collagen lattice contracted with fibroblast cells incorporated therein; and
   b. living glandular cells thereon or therein.

29. A gland-equivalent of claim 28 wherein said glandular cells comprise insulin-producing pancreatic cells.

* * * * *